(12) United States Patent
Rozet et al.

(10) Patent No.: US 9,487,782 B2
(45) Date of Patent: *Nov. 8, 2016

(54) METHODS FOR THE TREATMENT OF LEBER CONGENITAL AMAUROSIS

(71) Applicants: Jean-Michel Rozet, Paris (FR); Antoine Kichler, Evry (FR); Isabelle Perrault, Paris (FR); Josseline Kaplan, Paris (FR); Xavier Gerard, Paris (FR); Daniel Scherman, Paris (FR); M. Arnold Munnich, Paris (FR)

(72) Inventors: Jean-Michel Rozet, Paris (FR); Antoine Kichler, Evry (FR); Isabelle Perrault, Paris (FR); Josseline Kaplan, Paris (FR); Xavier Gerard, Paris (FR); Daniel Scherman, Paris (FR); M. Arnold Munnich, Paris (FR)

(73) Assignees: INSERM (Institut National de la Sante et de la Recherche Medicale), Paris (FR); CNRS (Centre National de la Recherche Scientifique), Paris (FR); GENETHON, Evry (FR); UNIVERSITE PARIS DESCARTES, Paris (FR); ENSCP—Chimie ParisTech—Ecole Nationale Superieure de Chimie de Paris, Paris (FR); Universite d'Evry-Val-d'Essonne, Evry (FR); ASSISTANCE PUBLIQUE HOPITAUX DE PARIS, Paris 4eme (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/546,124

(22) Filed: Nov. 18, 2014

(65) Prior Publication Data
US 2015/0111951 A1    Apr. 23, 2015

Related U.S. Application Data

(62) Division of application No. 14/125,063, filed as application No. PCT/EP2012/060906 on Jun. 8, 2012, now Pat. No. 9,012,425.

(30) Foreign Application Priority Data

Jun. 10, 2011 (EP) .................................. 11305735

(51) Int. Cl.
C07H 21/02 (2006.01)
C07H 21/04 (2006.01)
(Continued)

(52) U.S. Cl.
CPC ........... *C12N 15/113* (2013.01); *A61K 48/005* (2013.01); *C12N 2310/11* (2013.01); *C12N 2320/33* (2013.01); *C12N 2320/34* (2013.01)

(58) Field of Classification Search
USPC ............................................ 514/44; 536/24.5
See application file for complete search history.

(56) References Cited

U.S. PATENT DOCUMENTS

| 7,517,644 | B1 | 4/2009 | Smith |
| 2008/0044831 | A1 | 2/2008 | Hidebrandt |

(Continued)

FOREIGN PATENT DOCUMENTS

| WO | 2004/028458 A2 | 4/2004 |
| WO | 2004/048601 A2 | 6/2004 |
| WO | 2009/121536 A1 | 10/2009 |

OTHER PUBLICATIONS

Collin Rob W., et al., "Antisense Oligonucleotide (AON)-based Therapy for Cep290-associated LCA", Internet Citation, May 3, 2011, pp. 1-2, Retrieved from the Internet: URL:http//www.abstractsonline.com/plan/ViewAbstract.aspx?mID=2684&sKey=9456c86d-1d58-492c-ab4f-bc1dfbebebee&cKey=71c3af2e-9c21-4900-9e44-fd5d22b87025&mKey=%7B6F224A2D-AF6A-4533-8BBB-6A8D7B26EDB3%7D [retrieved on Mar. 30, 2012].

(Continued)

*Primary Examiner* — Terra C Gibbs
(74) *Attorney, Agent, or Firm* — Whitham, Curtis & Cook, P.C.

(57) ABSTRACT

The present invention relates to a method for treating a Leber congenital amaurosis in a patient harboring the mutation c.2991+1655 A>G in the CEP290 gene, comprising the step of administering to said patient at least one antisense oligonucleotide complementary to nucleic acid sequence that is necessary for preventing splicing of the cryptic exon inserted into the mutant c.2291+1655 A>G CEP290 mRNA.

4 Claims, 6 Drawing Sheets

Figure 1:
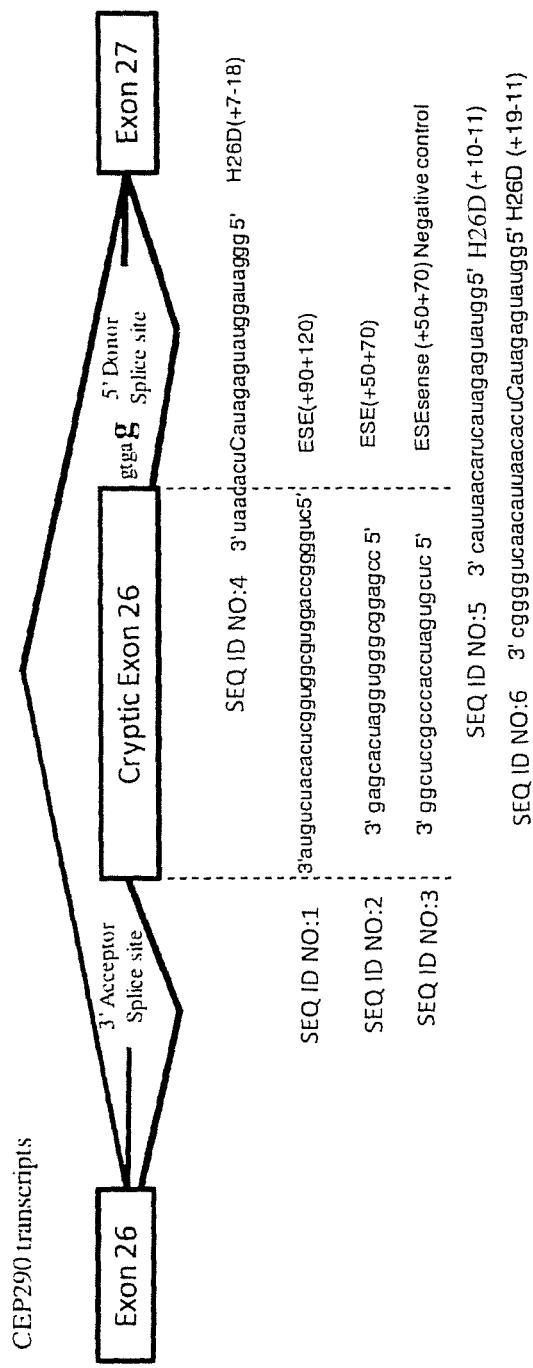

(51) Int. Cl.
   A61K 48/00    (2006.01)
   C12N 15/11    (2006.01)
   C12N 15/113   (2010.01)

(56) References Cited

U.S. PATENT DOCUMENTS

2014/0179767 A1*   6/2014   Rozet et al. ............... 514/44 A
2014/0336238 A1    11/2014  Collin et al.

OTHER PUBLICATIONS

Den Hollander Anneke I, et al., "Mutations in the CEP290 (NPHP6) gene are a frequent cause of leber congenital amaurosis", American Journal of Human Genetics, Sep. 2009, pp. 556-561, vol. 79, No. 3.

L. M. Baye, et al., "The N-terminal region of centrosomal protein 290 (CEP290) restores vision in a zebrafish model of human blindness", Human Molecular Genetics, Apr. 15, 2011, pp. 1467-1477, vol. 20, No. 8.

Artur V. Cideciyan, et al., "Centrosomal-ciliary geneCEP290/NPHP6 mutations result in blindness with unexpected sparing of photoreceptors and visual brain: implications for therapy of Leber congenital amaurosis", Human Mutation, Nov. 1, 2007, pp. 1074-1083, vol. 28, No. 11.

Gerard X, et al., "Antisense oligonucleotide-mediated exon skipping restores primary cilia assembly in fibroblasts harbouring the common LCA CEP290 c.2991+1655G>a mutation", Internet Citation, Aug. 31, 2011, p. 1, Retrieved from the Internet: http://www.ichg2011.org/cgi-bin/showdetail.pl?absno=10361 [retrieved on Mar. 30, 2012].

Collin et al., "Antisense oligonucleotide (AON)-based therapy for CEP290-associated LCA", Program No. 3324, Poster No. A572, May 3, 2011.

* cited by examiner

SEQUENCE LISTING

```
<160> NUMBER OF SEQ ID NOS: 6

<210> SEQ ID NO 1
<211> LENGTH: 31
<212> TYPE: RNA
<213> ORGANISM: Artificial
<220> FEATURE:
<223> OTHER INFORMATION: Synthetic antisense oligonucleotide AON ESE
      (+90+120)

<400> SEQUENCE: 1 cugggccag gugcgguggc ucacaucugu a                                    31

<210> SEQ ID NO 2
<211> LENGTH: 21
<212> TYPE: RNA
<213> ORGANISM: Artificial
<220> FEATURE:
<223> OTHER INFORMATION: Synthetic antisense oligonucleotide AON ESE
      (+50+70)

<400> SEQUENCE: 2
ccgaggcggg uggaucacga g                                              21

<210> SEQ ID NO 3
<211> LENGTH: 21
<212> TYPE: RNA
<213> ORGANISM: Artificial
<220> FEATURE:
<223> OTHER INFORMATION: Synthetic antisense oligonucleotide AON
      ESEsense (+50+70)

<400> SEQUENCE: 3
cucgugaucc acccgccucg g                                              21

<210> SEQ ID NO 4
<211> LENGTH: 25
<212> TYPE: RNA
<213> ORGANISM: Artificial
<220> FEATURE:
<223> OTHER INFORMATION: Synthetic antisense oligonucleotide AON
      H26D(+7-18)

<400> SEQUENCE: 4
gggauaggua ugagauacuc acaau                                          25

<210> SEQ ID NO 5
<211> LENGTH: 22
<212> TYPE: RNA
<213> ORGANISM: Artificial
<220> FEATURE:
<223> OTHER INFORMATION: Synthetic antisense oligonucleotide AON
      H26D(+10-11)

<400> SEQUENCE: 5
gguaugagau acucacaauu ac                                             22

<210> SEQ ID NO 6
<211> LENGTH: 31
```

```
<212> TYPE: RNA
<213> ORGANISM: Artificial
<220> FEATURE:
<223> OTHER INFORMATION: Synthetic antisense oligonucleotide AON
      H26D(+19-11)

<400> SEQUENCE: 6
gguaugagau acucacaauu acaacugggg c                              31
```

… …

METHODS FOR THE TREATMENT OF LEBER CONGENITAL AMAUROSIS

FIELD OF THE INVENTION

The present invention relates to the treatment of Leber congenital amaurosis. Particularly, exon skipping strategy is used.

BACKGROUND OF THE INVENTION

Leber congenital amaurosis (LCA, MIM204000) is a common cause of blindness in childhood (10%). It is the most severe inherited retinal dystrophy, responsible for blindness or profound visual deficiency at birth or in the first months of life. In the following months, the disease will either present as a dramatically severe and stationary cone-rod disease with extremely poor visual acuity (VA≤light perception; type I) or a progressive, yet severe, rod-cone dystrophy with measurable visual acuity over the first decade of life (20/200≤VA≤60/200; type II)[2].

Hitherto, alterations of 16 genes with highly variable patterns of tissular distribution and functions have been reported in LCA (Kaplan, J. Ophthalmic Genet. 29, 92-8 (2008); den Hollander, A I et al. Prog Retin Eye Res. 27, 391-419 (2008).). In Western countries, mutations affecting the centrosomal protein 290 (CEP290) are the main cause of the disease (20%) (den Hollander, A I et al. Am J Hum Genet. 79, 556-61 (2006); Perrault, I et al. Hum Mutat. 28, 416 (2007).). Among them, the c.2291+1655 A>G mutation accounts for over 10% of all cases, making this change an important target for therapy. The c.2291+1655 A>G mutation is located deep in intron 26 where it creates a splice-donor site 5 bp downstream of a strong cryptic acceptor splice site. As a result, a cryptic 128 bp exon which encodes a stop codon is inserted in the CEP290 mRNA, between exons 26 and 27 (den Hollander, A I et al. Am J Hum Genet. 79, 556-61 (2006)).

SUMMARY OF THE INVENTION

The present invention relates to a method for treating a Leber congenital amaurosis in a patient harbouring the mutation c.2991+1655 A>G in the CEP290 gene, comprising the step of administering to said patient at least one antisense oligonucleotide complementary to nucleic acid sequence that is necessary for preventing splicing of the cryptic exon inserted into the mutant c.2291+1655 A>G CEP290 mRNA

DETAILED DESCRIPTION OF THE INVENTION

Leber congenital amaurosis (LCA) is a severe hereditary retinal dystrophy responsible for congenital or early-onset blindness. The most common disease-causing mutation (>10%) is located deep in CEP290 intron 26 (c.2991+1655 A>G) where it creates a strong splice donor site and leads to the insertion of a cryptic exon encoding a premature stop codon. In the present invention, the inventors report data supporting the feasibility of an antisense oligonucleotide-mediated exon skipping strategy to correct splicing. The invention thus provides use of such exon-skipping strategy for the treatment of Leber congenital amaurosis.

The term "CEP290" has its general meaning in the art and refers to a protein encoded by the CEP390 gene. CEP290 is an integral component of the ciliary gate that bridges the transition zone between the cilia and cytoplasm. The protein plays an important role in maintaining the structural integrity of this gate, and thus has a crucial role in maintaining ciliary function (9. Craige, B et al. The Journal of Cell Biology. 190, 927-40 (2010).). The term may include naturally occurring "CEP290" and variants and modified forms thereof. The CEP290 can be from any source, but typically is a mammalian (e.g., human and non-human primate) CEP290, particularly a human CEP290. An exemplary native human CEP290 amino acid sequence is provided in GenPept database under accession number [EAW97414.1] and an exemplary native human nucleotide sequence encoding for CEP290 is provided in GenBank database under accession number [NM_025114.3].

A first object of the present invention relates to a method for restoring the function of CEP290 in a cell carrying the mutation c.2991+1655 A>G present in the CEP290 gene wherein said method comprises the step of preventing splicing of the cryptic exon inserted into the mutant c.2291+1655 A>G CEP290 mRNA.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein.

Particularly, the functionality of CEP290 can be measured by several methods recognized in the art. For example, improvement of cilia assembly and/or maintenance may be determined as described in the EXAMPLE.

Accordingly, the strategy of exon skipping as described above results in an amelioration of Leber congenital amaurosis symptoms (i.e. restoration of protein function or stability) in the range of at least about 10%, preferably about 20%, 30%, 40%, 50%, 60%, 70%, 80%, 90% or even 100%, compared to a non-treated patient case. Such symptoms may be observed on a micro level (i.e. restoration of protein expression and/or localisation evaluated by immunohistochemistry, immunofluorescence, Western-blot analyses; restoration/amelioration of protein functionality evaluated by the improvement of cilia assembly and/or maintenance, restoration/amelioration of cone functionality . . . ) or on a macro level (i.e. amelioration/restoration of clinical symptoms such as visual acuity).

Generally, the removal of the cryptic exon inserted into the mutant c.2291+1655 A>G CEP290 mRNA is carried out using anti-sense oligonucleotides (AONs)

The term "antisense oligonucleotide" refers to a single strand of DNA or RNA that is complementary to a chosen sequence. Antisense RNA can be used to prevent protein translation of certain mRNA strands by binding to them. Antisense DNA can be used to target a specific, complementary (coding or non-coding) RNA.

Oligonucleotides are designed to complement suitable sequences, usually RNA sequences within the pre-mRNA molecule which are required for correct splicing of the targeted exon, thereby blocking splicing reactions that would incorporate the targeted exon into mature mRNA. An AON typically binds to the sequence which it complements and sterically hinders the splicing reaction. Sequences are selected so as to be specific, i.e. the AON's are complementary only to the sequences of the pre-mRNA and not to other nucleic acid sequences. The AON's used in the practice of the invention may be of any suitable type, e.g. oligodeoxyribonucleotides, oligoribonucleotides, morpholinos, tricyclo-DNA-antisense oligonucleotides, U7- or U1-mediated AONs or conjugate products thereof such as peptide-conjugated or nanoparticle-complexed AONs. AONs employed in the practice of the invention are generally from about 10 to about 50 nucleotides in length, and may be for example, about 10 or fewer, or about 15, or about 20 or about 30 nucleotides or more in length. The optimal length of the AON's for a targeted complementary sequence is generally in the range of from about 15 to about 30 nucleotides long depending on the chemical backbone used and on the target sequence. Typically, morpholino-AONs are about 25 nucleotides long, 2'PMO-AONs are about 20 nucleotides long, and tricyclo-AONs are about 15 nucleotides long.

In a particular embodiment, two or even more AONs can also be used at the same time; this may be particularly interesting when the AON are vectorized within an expression cassette (as for example by U7 or U1 cassettes).

Accordingly a further object of the invention relates to an antisense oligonucleotide complementary to a nucleic acid sequence of CEP290 gene that is necessary for correct splicing of the cryptic exon inserted into the mutant c.2291+ 1655 A>G CEP290 mRNA.

In a particular embodiment, the antisense oligonucleotides comprises a nucleic acid sequence selected from the group consisting of SEQ ID NO:1 (ESE(+90+120)), SEQ ID NO:2 (ESE(+50+70)), SEQ ID NO:4 (H26D(+7−18)), SEQ ID NO:5 (H26D(+10−11)) and SEQ ID NO:6 (H26D(+19− 11)). Typically, said antisense oligonucleotides have a length of at least 15 nucleotides.

In a more particular embodiment, said antisense oligonucleotide may be selected from the group consisting of sequences SEQ ID NO:1 (ESE(+90+120)), SEQ ID NO:2 (ESE(+50+70)), SEQ ID NO:4 (H26D(+7−18)), SEQ ID NO:5 (H26D(+10−11)) and SEQ ID NO:6 (H26D(+19−11)).

A combination of said antisense oligonucleotides may also be used according to the invention for correct splicing of the cryptic exon inserted into the mutant c.2291+1655 A>G CEP290 mRNA.

For use in the instant invention, the AONs of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, AON's can be produced on a large scale in plasmids (see Sambrook, et al., 1989). AON's can be prepared from existing nucleic acid sequences using known techniques, such as those employing restriction enzymes, exonucleases or endonucleases. AON's prepared in this manner may be referred to as isolated nucleic acids.

For use in vivo, the AONs may be or are stabilized. A "stabilized" AON refers to an AON that is relatively resistant to in vivo degradation (e.g. via an exo- or endo-nuclease). Stabilization can be a function of length or secondary structure. Alternatively, AON stabilization can be accomplished via phosphate backbone modifications. Preferred stabilized AON's of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AON's also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

In a particular embodiment, the antisense oligonucleotides of the invention may be 2'-O-Me RNA/ENA chimera oligonucleotides (Takagi M, Yagi M, Ishibashi K, Takeshima Y, Surono A, Matsuo M, Koizumi M. Design of 2'-O-Me RNA/ENA chimera oligonucleotides to induce exon skipping in dystrophin pre-mRNA. Nucleic Acids Symp Ser (Oxf). 2004; (48):297-8).

Other forms of AONs that may be used to this effect are AON sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

In another particular embodiment, the antisense oligonucleotides of the invention are 2'-O-methyl-phosphorothioate nucleotides.

A further object of the present invention relates to a method for treating a Leber congenital amaurosis in a patient harbouring the mutation c.2991+1655 A>G in the CEP290 gene, comprising the step of administering to said patient at least one antisense oligonucleotide complementary to nucleic acid sequences that are necessary for preventing splicing of the cryptic exon inserted into the mutant c.2291+ 1655 A>G CEP290 mRNA.

In a particular embodiment, the invention relates to said method wherein antisense oligonucleotide is complementary to a nucleic acid sequence that is necessary for preventing splicing of the cryptic exon inserted into the mutant c.2291+ 1655 A>G CEP290 mRNA.

In a particular embodiment, the antisense oligonucleotides comprises a nucleic acide sequence selected from the group consisting of SEQ ID NO:1 (ESE(+90+120)), SEQ ID NO:2 (ESE(+50+70)), SEQ ID NO:3 (H26D(+7−18)), SEQ ID NO:4 (H26D(+10−11)) and SEQ ID NO:5 (H26D(+19− 11)). Typically, said antisense oligonucleotides have a length of at least 15 nucleotides.

In a more particular embodiment, said antisense oligonucleotide may be selected from the group consisting of sequences SEQ ID NO:1 (ESE(+90+120)), SEQ ID NO:2 (ESE(+50+70)), SEQ ID NO:3 (H26D(+7−18)), SEQ ID NO:4 (H26D(+10−11)) and SEQ ID NO:5 (H26D(+19−11)). In a particular embodiment a combination of said antisense oligonucleotides may also be used.

The invention further relates to an antisense oligonucleotide of the invention for the treatment of Leber congenital amaurosis in a patient harbouring the mutation c.2991+1655 A>G in the CEP290 gene.

In a particular embodiment; antisense oligonucleotides of the invention may be delivered in vivo alone or in association with a vector. In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Preferred viral vectors according to the invention include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected through an intraocular way (intravitreal, sub retinal, suprachoroidal . . . ). It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide nucleic acid sequence is under the control of a heterologous regulatory region, e.g., a heterologous promoter. The promoter can also be, e.g., a viral promoter, such as CMV promoter or any synthetic promoters.

The present invention also provides a pharmaceutical composition containing an antisense oligonucleotide of the invention (or a vector of the invention) for the treatment of a Leber congenital amaurosis in a patient harbouring the mutation c.2991+1655 A>G in the CEP290 gene.

Pharmaceutical compositions of the present invention may also include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. Those of skill in the art will also recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

Typically, the antisense oligonucleotides of the invention (or vectors of the invention) may be delivered in a pharmaceutically acceptable ophthalmic vehicle, such that the antisense oligonucleotide of the invention (or vectors of the invention) can penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the antisense oligonucleotides of the invention (or vectors of the invention) may be injected directly into the vitreous, aqueous humour, ciliary body tissue(s) or cells and/or extra-ocular muscles, retina (e.g. after retinal detachment) or even in the suprachoroidal space. Electroporation or sonoporation means may also be suitable for delivering the antisense oligonucleotides of the invention (or vectors of the invention).

One skilled in the art will recognize that the amount of an AON to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.).

If a viral-based delivery of AONs is chosen, suitable doses will depend on different factors such as the viral strain that is employed, the route of delivery (intramuscular, intravenous, intra-arterial or other).

Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the AONs of the invention will likely be administered on multiple occasions, that may be, depending on the results obtained, several days apart, several weeks apart, or several months apart, or even several years apart. This is especially true where the treatment of Leber congenital amaurosis is concerned since the disease is not cured by this treatment, i.e. the gene that encodes the protein will still be defective and the encoded protein will still possess an unwanted, destabilizing feature such as an exposed proteolytic recognition site, unless the AONs of the invention are administered.

The invention will be further illustrated by the following figures and examples. However, these examples and figures should not be interpreted in any way as limiting the scope of the present invention.

FIGURES

FIG. 1 Schematic representation of wild-type and mutant CEP290 transcripts and sequences of AONs. Four AONs were designed to target ESE sequences in the cryptic exon using the ESEfinder 3.0 program available at http://rulai.c-shl.edu/cgi-bin/tools/ESE3/.

Figure 2A:
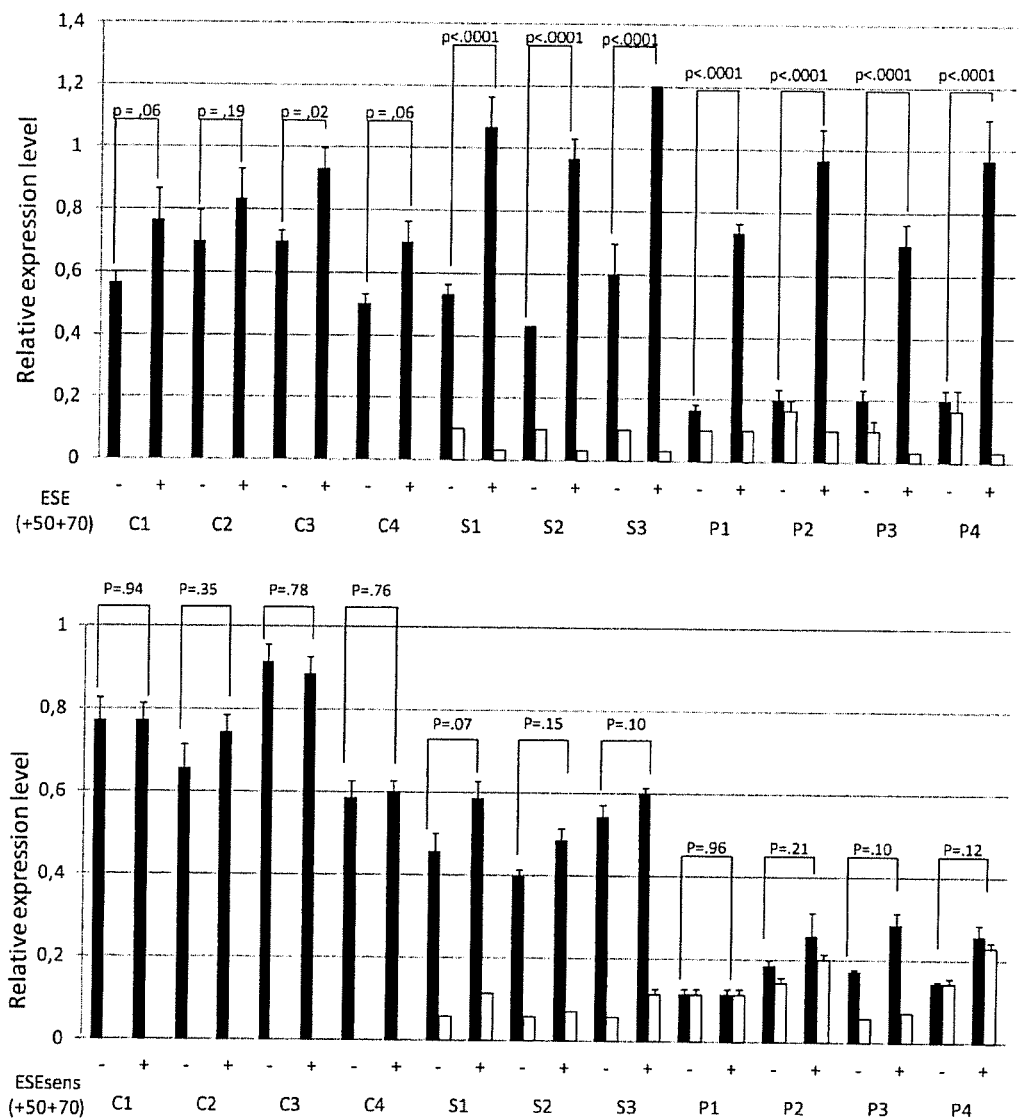
Figure 2B:
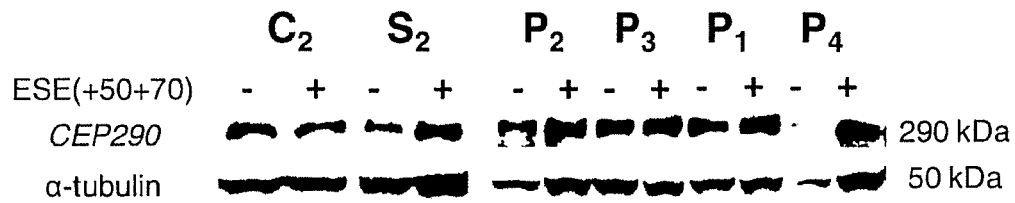
Figure 2B:
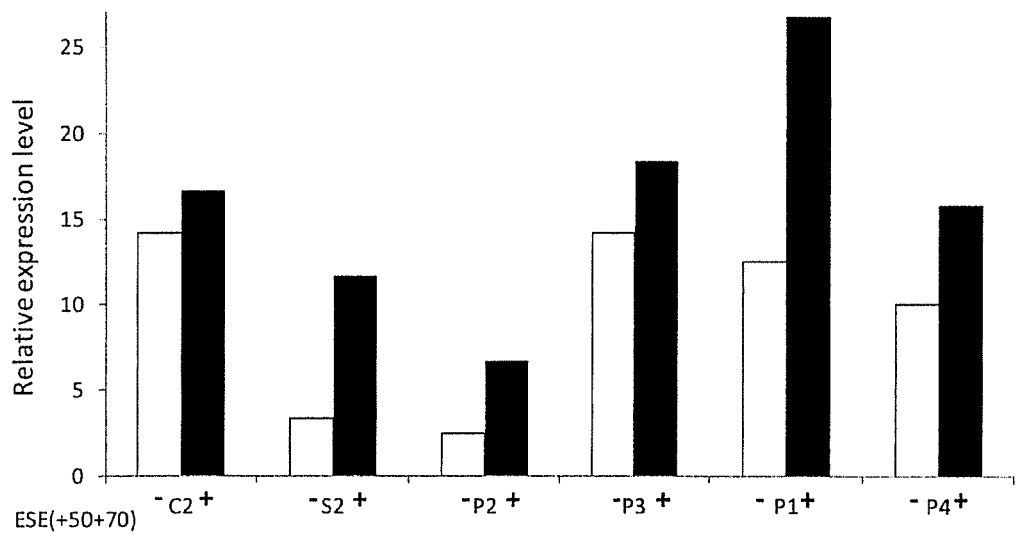
Figure 2B:
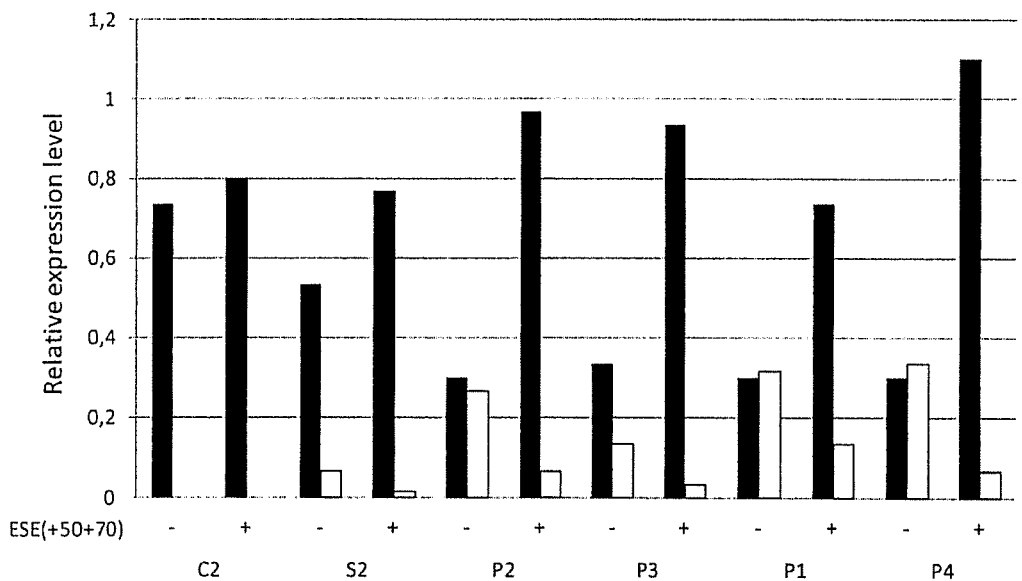
Figure 2C:
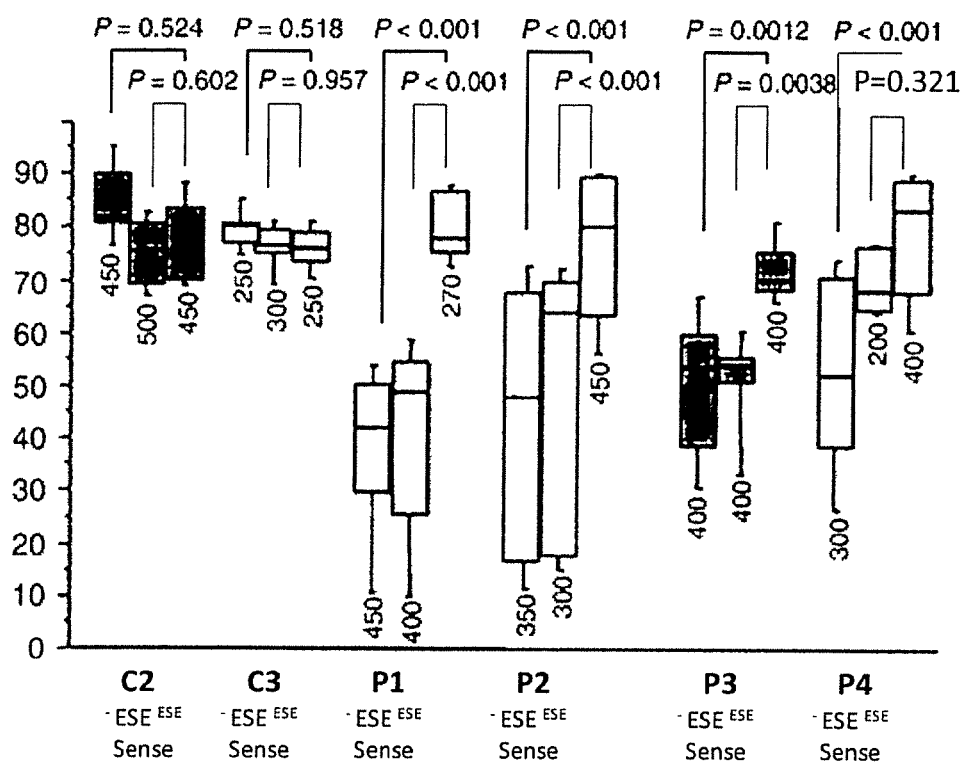

FIG. 2A-C Effect of AON-mediated exon skipping of the mutant cryptic CEP290 exon on messenger RNAs, protein and primary cilia expression. All measures were recorded in treated (+) or untreated (−) fibroblasts derived from skin biopsies of control individuals ($C_1$-$C_4$), heterozygous unaffected carriers ($S_1$-$S_3$) and/or patients ($P_1$-$P_4$). The error bars represent the standard deviation of the mean from three independent experiments. a) Relative expression levels of wild-type (plain bars) and c.2291+1655 A>G mutant (hatched bars) messengers were determined by RT-qPCR. Results were normalized using the software geNorm taking as reference the RPLP0 and GUSB genes or TBP, RPLP0 and GUSB. Basal expression levels of wild-type CEP290 messengers were strikingly reduced in patients' cell lines compared to controls. Transfections with the antisense but not the sense oligonucleotide ESE(+50+70) (upper and lower panels, respectively) resulted in a statistically significant increase in the expression of the CEP290 wild-type allele in patients and heterozygous carriers (p<0.0001). b) Correlation between the mutant messenger knock-down and the synthesis of the wild-type CEP290 protein. The expression of the CEP290 proteins in cell lines before (−) and after treatment (+) with the AON ESE (+50+70) was determined by Western blot. The relative variations in CEP290 concentrations (central panel) were determined by computed-densitometry analysis of CEP290 and α-tubulin expression in each sample. RT-qPCR analysis of patient samples used for Western blot analysis confirmed efficient exon-skipping in all treated cell lines (lower panel). The results of RT-qPCR were normalized by the software geNorm taking as reference three genes TBP, RPLP0 and GUSB. c) Effect of exon-skipping on the ciliogenesis. Nuclei, cilia and basal bodies of untreated cell lines and fibroblasts transfected with the ESE(+50+70) and ESEsense (+50+70) oligonucleotides were stained using DAPI (blue), anti-acetylated-tubulin (green) and anti-γ-tubulin (red) antibodies, respectively (right panel). The proportions of fibroblasts presenting a primary cilium among cells were calculated by numbering at least 200 cells (individual numbers are given under each bars; left panel). The error bars represent the Standard deviation from counts of at least 4 fields (mean n=9) recorded from two independent experiments. AON-mediated exon skipping of the mutant cryptic CEP290 exon on messenger RNAs resulted in increased proportions of cells harbouring a primary cilium for the four patients (statistically significant in ¾ patients' cell lines P1, P2, P3).

Figure 3A:
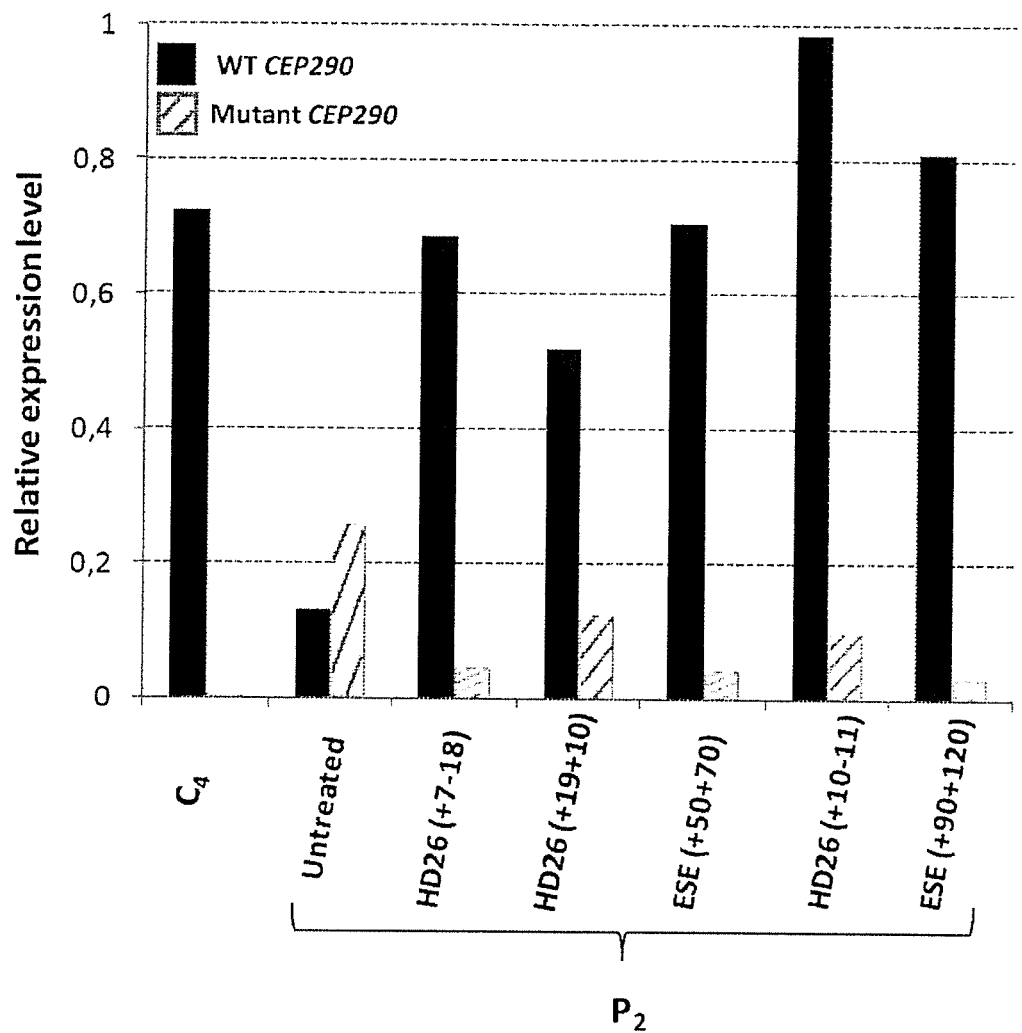
Figure 3B:
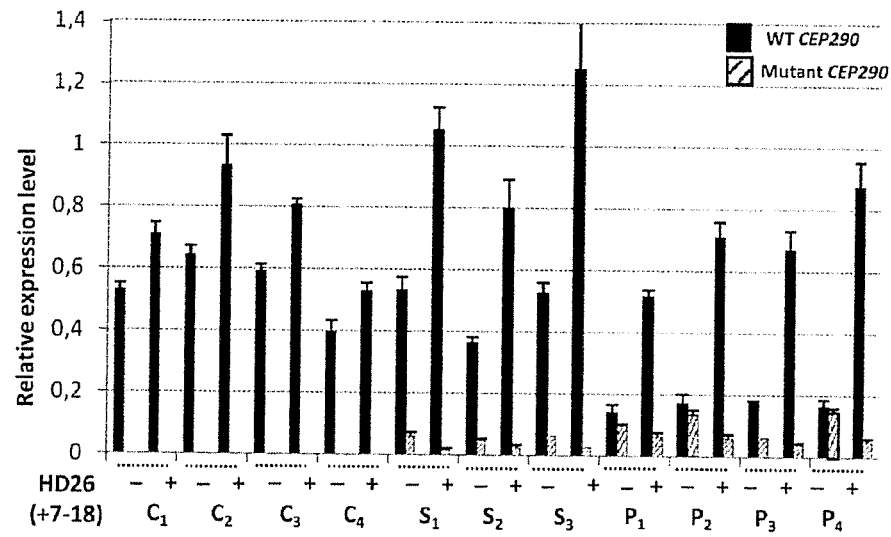
Figure 3B:
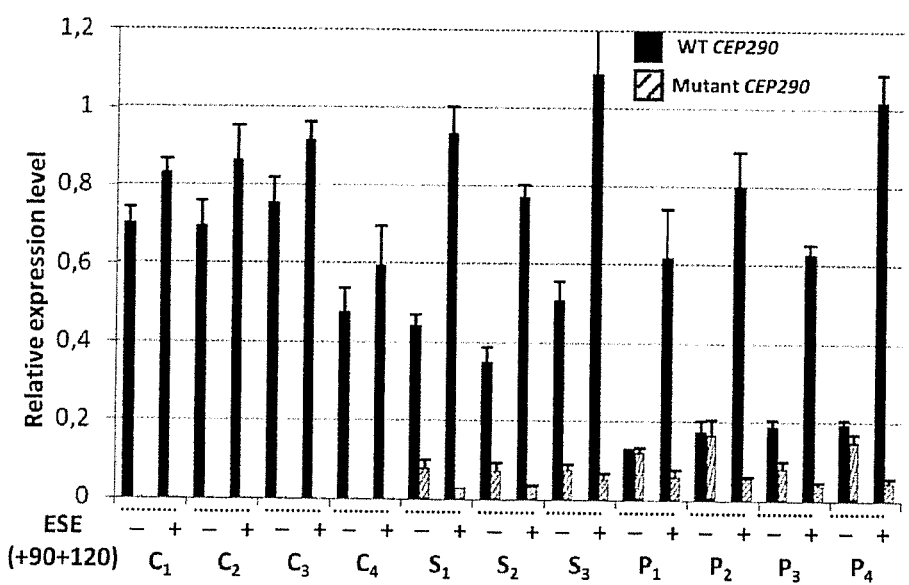

FIG. 3A-B. (a) Expression of wild-type transcripts and mutant (c.2991 1655 A>G) of the CEP290 gene in cells of patient (P2) and control (C4) after transfection or not (=condition "untreated") of five different antisense oligonucleotides. The results of RT-qPCR were normalized using geNorm software and using as reference the two following genes: GUSB and RPLP0. The graph shows the amounts of transcribed wild-type (WT CEP290, black bars) and mutant (Mutant CEP290, hatched bars). (b) Effectiveness of skipping of exon cryptic on the CEP290 messenger RNA mutants. All measurements were performed on untransfected cells (−) or transfected (+) by antisense oligonucleotides HD26 (7-18) and ESE (90 120). Cells used are fibroblasts derived from healthy individuals (C1-C4), heterozygous carriers of non-patients (S1-S3) and individuals with LCA (P1-P4). The error bars represent the standard deviation of the average derived from three independent experiments. The expression levels of mRNA wild-type (WT CEP290, black bars) and mutant 1655 c.2991 A>G (Mutant CEP290; hatch bars) were determined by RT-qPCR. The results were normalized using geNorm logicile and using as reference genes RPLP0 and GUSB.

EXAMPLE 1

Antisense Oligonucleotide-Mediated Exon Skipping Allows Efficient Correction of Abnormal CEP290 Splicing in Leber Congenital Amaurosis Due to the Frequent CEP290 C.2291+1655A>G Mutation Materials and Methods:
Transfection Agent and AONs:
The 26 residues long cationic transfecting peptide LAH4-L1[1] was prepared by automated solid-phase synthesis on Millipore 9050 or ABI 431 synthesizers using fmoc chemistry (a kind gift by A J Mason and B. Bechinger). The transfection agents Lipofectamine2000 and DOTAP were obtained from (Invitrogen) and (Sigma-Aldrich), respectively. The 2'-O-methylphosphorothioate oligonucleotides were obtained from Sigma.

Cell Culture and AON Transfection:
Skin biopsies were obtained from 4 LCA patients harbouring the c.2291+1655 A>G mutation (¾ homozygous, P1, P2, P4; ¼ compound heterozygous with the c.5850delT, p.Phe1950LeuFsX14 mutationP3) 3 heterozygous unaffected carriers ($S_1$ to $S_3$) and control individuals ($C_1$ to $C_4$). Written consent was obtained for each individual and research was approved by Institutional review board.

Primary fibroblasts were isolated by selective trypsinisation and proliferated at 37° C., 5% $CO_2$ in Opti-MEM Glutamax I medium (Invitrogen) supplemented with 10% fetal bovine serum (Invitrogen), 1% ultroser G substitute serum (Pall France) and 1% streptomycin/penicillin (Invitrogen). Fibroblasts between passage 7 and 9 were plated at $4\times10^5$ cells/well in 6-well plates 24 hours before transfection. Cells at a confluence of 80% were transfected with 2'-OMePS AONs (150 nM) in Opti-MEM using LAH4-L1 at a 1:10 (w:w) AON:peptide ratio. After 3 hours of incubation at 37° C., the transfection medium was replaced by fresh culture medium.

For the inhibition of nonsense mediated decay, 25 µg/ml of emetine dihydrochloride hydrate (Sigma-Aldrich) was added to the medium for 12 hours.

RNA Extraction and cDNA Synthesis:

Twenty four hours after transfection, the transfected and untreated cells were recuperated. Total RNA was extracted using the RNeasy Mini Kit (Qiagen) according to manufacturer's protocol. All samples were DNase treated by the RNase-free DNase set (Qiagen). Concentration and purity of total RNA was assessed using the Nanodrop-8000 spectrophotometer (Nanodrop Technologies) before storage at −80° C. Qualitative analysis of total RNA was performed using the Bioanalyzer 2220 (RNA 6000 Nano kit; Agilent) to verify that the RIN was between 8 and 10. First-stranded cDNA synthesis was performed from 500 ng of total RNA extracted using Verso cDNA kit (Thermo Fisher Scientific) with Random Hexamer:Anchored Oligo(dT) primers at a 3:1 (v:v) ratio according to the manufacturer's instructions. A non-RT reaction (without enzyme) for one sample was used as control and also analyzed by qPCR.

Reverse Transcription Quantitative PCR (RT-qPCR):

To measure the level of expression of CEP290 messengers, the wild-type and mutant alleles were amplified as 93 pb and 117 bp fragments, respectively. Regions of 132 pb, 80 bp, 84 bp, 101 bp and 95 bp within the human TATA box-binding protein mRNA (TBP, NM_003194), the human beta-2-microglobulin mRNA (B2M, NM_004048.2), the human beta glucuronidase mRNA (GUSB, NM_000181.3), the human hypoxanthine phosphoribosyltransferase 1 mRNA (HPRT1, NM_000194) and the human P0 large ribosomal protein mRNA (RPLP0, NM_001002.3) were used for normalization, respectively. A 99 pb fragment of the human albumin gene (ALB, NM_000477) was used to control the non-contamination of cDNAs by genomic DNA. Primers were designed using the Oligo Primer Analysis Software v.7 available at http://oligo.net. The specificity of primer pairs to PCR template sequences was checked against the NCBI database using the Primer-BLAST software available at www.ncbi.nlm nih.gov/tools/primer-blast.

cDNAs (5 µl of a 1:25 dilution in nuclease-free water) were subjected to real-time PCR amplification in a buffer (20 µl) containing MESA BLUE qPCR Master Mix Plus for Sybr Assay (Eurogentec) and 300 nM of forward and reverse primers, on a Taqman 7900 HT Fast Real-Time PCR System (Applied Biosystems) under the following conditions: initial denaturation at 95° C. for 5 min, followed by 50 cycles of 15 sec at 95° C. and 1 min at 65° C. The specificity of amplification products was determined from melting curve analysis performed at the end of each run using a cycle at 95° C. for 15 sec, 65° C. for 15 sec and 95° C. for 15 sec. Data were analyzed using the SDS 2.3 software (Applied Biosystems).

For each cDNA sample, the mean of quantification cycle (Cq) values was calculated from triplicates (standard deviation SD<0.5 Cq). CEP290 Expression levels were normalized to the "normalization factor" obtained from the geNorm software for Microsoft Excel$^2$ which uses the most stable reference genes and amplification efficiency estimates calculated for each primer-pair using 4-fold serial dilution curves (1:5, 1:25, 1:125, 1:625). No reverse transcriptase (non-RT), no template (NTC) reactions and non-contamination of cDNAs by genomic DNA (ALBh) were used as negative controls in each run (Cq values NTC=Undetermined, non-RT>40 and ALBh>40).

The quantitative data are the means±SEM of three independent experiments and these are presented as ratio among values for individual mRNAs. The significance of variations among samples was estimated using the Protected List Significant Difference (PLSD) of Fisher according to the significance of analysis of variance (ANOVA test).

Western Blot Analysis:

24 h after transfection cells were harvested and submitted to lysis in a Triton/SDS buffer (25 mM Tris-base pH7.8, 1 mM DTT, 1 mM EDTA, 15% Glycerol, 8 mM $MgCl_2$, 1% Triton and 1% SDS) containing complete protease inhibitor cocktail (Roche) on ice for 30 min with repeated mixing. Released DNA was fragmented by 20 s of Ultra-turrax homogenizer (Ika-Werke) and the lysates were centrifuged (15000 g at 4° C. for 10 min). Protein concentrations were determined from the detergent-soluble fractions using the DC™ Protein Assay kit according to the manufacturer protocol (Bio-Rad). Proteins (125 µg) were denatured at 90° C. for 10 minutes in 4× premixed protein sample buffer (XT sample Buffer, Biorad) and separated by electrophoresis (50 volts for 30 minutes followed by 140 volts for 90 minutes at room temperature) on NuPAGE 3-8% Tris Acetate gels (Invitrogen). Proteins were transferred (100 volts, 2 h at 4° C.) to Immobilon-P PVDF membranes (Millipore). Membranes were blocked with PBS 0.5% Tween-20/5% dry milk powder and incubated over night at 4° C. under agitation with polyclonal rabbit anti-human CEP290 (Novus Biologicals) or monoclonal mouse anti-α-tubulin (Sigma) primary antibodies in 1:1800 and 1:500000 dilutions, respectively. Membranes were washed three times in PBS 0.5% Tween-20 solution (15 min) and incubated for 1 hour at room temperature with HRP-conjugated donkey anti-rabbit and sheep anti-mouse immunoglobulins secondary antibodies (Amersham GE Healthcare) in 1:10000 dilutions, respectively. ECL Western Blotting Detection Reagents (Amersham GE Healthcare) was applied according to the manufacturer's instructions and the blot was exposed to Amersham Hyperfilm ECL (Amersham GE Healthcare). The relative expression of the CEP290 protein was estimated by densitometry using α-tubulin as reference on a G:Box from Syngene with the GeneSnap and GeneTool Softwares.

Flow Cytometry:

ESEsense(+50+70)) and antisense ESE (+50+70) AON carrying a 3' end fluorescein group were obtained from Sigma. Fibroblasts were transfected as described previously. After 3 h of incubation, cells were trypsinated, washed twice in PBS, and maintained into PBS containing 3% serum. Cells were analysed on a Facscalibur flow cytometer (Becton Dickinson, Grenoble, France) using the software CELL-Quest. Percentages of fluorescent cells were calculated from 20,000 morphologically intact cells.

Immunofluorescence Microscopy:

Fibroblasts were seeded at $2.5 \times 10^5$ cells/well on glass coverslips in 12-well plates. 24 hours before transfection with the ESEsense (+50+70) and ESE (+50+70) AONs, in the conditions described previously. Ten hours after transfection, cells were washed with PBS and incubated 30 h in serum free medium (37° C., 5% CO2). Untreated fibroblasts were processed in the same conditions. Subsequently, cells were fixed in ice-cold methanol (5 minutes at −20° C.) and washed twice in PBS. Cells were permeabilized in PBS supplemented with 3% BSA and 0.1% Triton for 1 hour at room temperature before being incubated overnight at 4° C. in permeabilization buffer containing (rabbit anti-γ-tubulin (1:1000), mouse monoclonal anti-acetylated tubulin (1:1000); Sigma-Aldrich) primary antibodies. After three washes with PBS, cells were incubated for 1 hour at room temperature in permeabilization buffer containing secondary antibodies (Alexa-Fluor 594- and Alexa-Fluor 488-conjugated goat anti-rabbit IgG (1:1000) and goat anti-mouse IgG (1:1000); Molecular Probes) followed by three washes PBS. A mounting media containing DAPI (DAPI Fluoromount G; SouthernBiotech) was used to label nuclei. Immunofluorescence images were obtained using a Leica DM IRBE microscope and a MicroPublisher 3.3 RTV camera (Q-Imaging). The final images were generated using the Cartograph version 7.2.3 (Microvision Instruments) and ImageJ (National Institutes of Health). The percentage of ciliated cells was calculated from two independent experiments (n>300 cells for each cell line). The significance of variations among samples was estimated using the PLSD of Fisher according to the significance of the ANOVA test.

Results

Leber congenital amaurosis (LCA, MIM204000) is a common cause of blindness in childhood (10%)[1]. It is the most severe inherited retinal dystrophy, responsible for blindness or profound visual deficiency at birth or in the first months of life. In the following months, the disease will either present as a dramatically severe and stationary cone-rod disease with extremely poor visual acuity (VA≤light perception; type I) or a progressive, yet severe, rod-cone dystrophy with measurable visual acuity over the first decade of life (20/200≤VA≤60/200; type II)[2].

Hitherto, alterations of 16 genes with highly variable patterns of tissular distribution and functions have been reported in LCA[1,3]. In Western countries, mutations affecting the centrosomal protein 290 (CEP290) are the main cause of the disease (20%)[4,5]. Among them, the c.2291+1655 A>G mutation accounts for over 10% of all cases, making this change an important target for therapy.

The c.2291+1655 A>G mutation is located deep in intron 26 where it creates a splice-donor site 5 bp downstream of a strong cryptic acceptor splice site (FIG. 1). As a result, a cryptic 128 bp exon which encodes a stop codon is inserted in the CEP290 mRNA, between exons 26 and 27[4]. Considering the great potential of exon skipping as a therapy to by-pass protein-truncating gene lesions[6,7], we assessed the possibility to use antisense oligonucleotides (AON) to hide the cryptic donor splice site created by the c.2291+1655 A>G mutation from the splicing machinery, and correct the abnormal splicing in carrier patients' cell lines.

Fibroblasts were derived from skin biopsies of controls (C1-C4), unaffected heterozygous carriers (S1-S3) and homozygous (P1, P2 and P4) or compound heterozygous (P3) patients.

The efficiency of the skipping strategy was assessed after optimizing 2'O-methyl phosphorothioate-modified AON sequences (FIG. 1) and concentrations, transfection conditions and treatment time (not shown). Expression levels of the wild-type and mutant CEP290 mRNAs were measured by quantitative reverse transcription PCR (RT-qPCR) in untreated fibroblasts and cells transfected with an AON designed to target exon splicing enhancer (ESE) sequences (ESE(+50+70)) or a sense version (ESEsense(+50+70)).

Untreated patient's fibroblasts expressed significantly reduced levels of the wild-type CEP290 allele compared to controls and heterozygous carriers (FIG. 2a). When the cells were transfected with the AON ESE(+50+70), patients, unaffected carriers and controls fibroblasts expressed the wild-type messengers to equivalent levels, suggesting highly efficient skipping of the mutant cryptic exon (FIG. 2a). The increase in expression of the wild-type allele was strikingly higher than the decrease in expression of the mutant allele. These data suggested the degradation of mutant messengers through cellular mRNA control quality processes, in particular nonsense mediated decay (NMD). The significant increase of the mutant but not the wild-type mRNA levels in the fibroblasts of a homozygous patient (P1) treated with the NMD inhibitor emetine[8] gave strong support to this hypothesis.

The splicing was unchanged when cell lines were treated with the sense oligonucleotide (FIG. 2a). To ascertain that the absence of effect of the sense version of the AON on CEP290 splicing was not due to a reduced delivery efficiency, the cell line of Patient P1 was transfected using fluorescently labeled sense and antisense ESE(+50+70) AONs, respectively. Evidence for similar transfection efficiencies with both AONs gave strong support to the sequence-dependent skipping of the CEP290 cryptic exon. In this regard, it is worth noting that similar levels of skipping were reached when cell lines were treated with an antisense AONs designed to target an ESE site predicted downstream of the +50+70 sequence (ESE(+90+120)) (FIG. 1). These data indicate that different AONs may allow efficient skipping of the cryptic exon inserted into the mutant c.2291+1655 A>G CEP290 mRNA.

Three other AON were identified (Table 1) which are able to induce exon skipping.

TABLE 1

Sequence of the 2'OMe-PS Oligonucleotides

| AON | Sequence |
| --- | --- |
| H26D (+10-11) | 5'- gguaugagauacucacaa uuac -3 (SEQ ID NO: 5) |
| H26D (+19-11) | 5'- gguaugagauacucacaa uuacaacuggggc -3' (SEQ ID NO: 6) |
| H26D (+7-18) | 5'- gggauagguaugagauac ucacaau -3 (SEQ ID NO: 4) |

To determine whether AON-induced exon skipping in the fibroblasts of patients influenced CEP290 protein levels, we performed Western blot analysis using a polyclonal antibody recognizing the C-terminus of the CEP290 protein. Increased levels of the wild-type CEP290 protein were evidenced when the cell lines of patients and unaffected carriers were treated with the antisense oligonucleotide but not the sense version.

CEP290 is an integral component of the ciliary gate that bridges the transition zone between the cilia and cytoplasm. The protein plays an important role in maintaining the structural integrity of this gate, and thus has a crucial role in maintaining ciliary function[9]. We previously reported that nasal epithelial cells of LCA patients harbouring CEP290 mutations, including the c.2991+1655A>G change, present short cilia and heterogeneous axonemal abnormalities suggestive of a defect in cilia assembly or maintenance[10]. Here, we show that following serum-starvation, primary cilia expression is significantly reduced in LCA patients' fibroblasts harbouring the c.2991+1655A>G change compared to control cell lines (mean$_{P1-P4}$=48.6%±6.5% versus mean$_{C1,C3}$=83.6%±3.2%; p=0.0097; FIG. 2c).

Interestingly, upon transfection with the AON ESE(+50+70) but not the ESEsense(+50+70) oligonucleotide, the proportion of ciliated patients' cells increased significantly, reaching levels similar to controls: mean$_{P1-P4+ESE(+50+70)}$=75.3%±3.5% vs mean$_{P1-P4+ESEsense(+50+70)}$=58.75%±8.77%, p<0.01; mean$_{P1-P4+ESE(+50+70)}$ vs mean$_{C1,C3+ESE(+50+70)}$=78.3%±3.4%; p=0.624 (FIG. 2c). This suggests that AON-mediated exon skipping resulted in a significant improvement of cilia assembly and/or maintenance.

CEP290 mutations are the most common cause of LCA, yet no curative treatment exists. Our present results show therapeutic potential of exon skipping for the treatment of the mutation c.2291+1655A>G which accounts alone for 10% of all LCA cases.

REFERENCES

Throughout this application, various references describe the state of the art to which this invention pertains. The disclosures of these references are hereby incorporated by reference into the present disclosure.

The invention claimed is:

1. A method for restoring the function of CEP290 in a cell carrying the mutation c.2991+1655 A>G present in the CEP290 gene wherein said method comprises the step of preventing splicing of the cryptic exon inserted into the mutant c.2291+1655 A>G CEP290 mRNA by using at least one antisense oligonucleotide that is complementary to a sequence within the mutant c.2991+1655 A>G CEP290 pre-mRNA which is required for correct splicing of said targeted cryptic exon, wherein said sequence is selected from the group consisting of exon splicing enhancer (ESE) sequences and a sequence comprising the donor splice site created by the c.2991+1655 A>G mutation, and wherein said antisense oligonucleotide consists of a nucleic acid sequence selected from the group consisting of SEQ ID NO:1 (ESE(+90+120)), SEQ ID NO:2 (ESE(+50+70)), SEQ ID NO:4 (H26D(+7-18)), SEQ ID NO:5 (H26D(+10-11)) and SEQ ID NO:6 (H26D(+19-11)).

2. A modified antisense oligonucleotide which induces exon-skipping and consists of a sequence complementary to a nucleic acid sequence of CEP290 gene that is necessary for correct splicing of the cryptic exon inserted into the mutant c.2291+1655 A>G CEP290 mRNA, wherein said nucleic acid sequence of CEP290 gene is selected from the group consisting of exon splicing enhancer (ESE) sequences and a sequence comprising the donor splice site created by the c.2991+1655 A>G mutation, and wherein said antisense oligonucleotide consists of a nucleic acid sequence selected from the group consisting of SEQ ID NO:1 (ESE(+90+120)), SEQ ID NO:2 (ESE(+50+70)), SEQ ID NO:4 (H26D(+7-18)), SEQ ID NO:5 (H26D(+10-11)) and SEQ ID NO:6 (H26D(+19-11)).

3. A pharmaceutical composition comprising at least one modified antisense oligonucleotide according to claim 2.

4. A method for treating a Leber congenital amaurosis in a patient harbouring the mutation c.2991+1655 A>G in the CEP290 gene wherein said method comprises the step of preventing splicing of the cryptic exon inserted into the mutant c.2291+1655 A>G CEP290 mRNA by using at least one antisense oligonucleotide that is complementary to a sequence within the mutant c.2991+1655 A>G CEP290 pre-mRNA which is required for correct splicing of said targeted cryptic exon, wherein said sequence is selected from the group consisting of exon splicing enhancer (ESE) sequences and a sequence comprising the donor splice site created by the c.2991+1655 A>G mutation, and wherein said antisense oligonucleotide consists of a nucleic acid sequence selected from the group consisting of SEQ ID NO:1 (ESE(+90+120)), SEQ ID NO:2 (ESE(+50+70)), SEQ ID NO:4 (H26D(+7-18)), SEQ ID NO:5 (H26D(+10-11)) and SEQ ID NO:6 (H26D(+19-11)).

* * * * *